United States Patent
Isaacs

(10) Patent No.: US 9,821,131 B2
(45) Date of Patent: Nov. 21, 2017

(54) INTUBATION DEVICE

(71) Applicant: Innovative Premiums, Inc., Oceanside, NY (US)

(72) Inventor: Judah Isaacs, Oceanside, NY (US)

(73) Assignee: INNOVATIVE PREMIUMS, INC., Oceanside, NY (US)

( * ) Notice: Subject to any disclaimer, the term of this patent is extended or adjusted under 35 U.S.C. 154(b) by 566 days.

(21) Appl. No.: 14/464,842

(22) Filed: Aug. 21, 2014

(65) Prior Publication Data

US 2016/0051781 A1    Feb. 25, 2016

(51) Int. Cl.
| | |
|---|---|
| *A61M 16/04* | (2006.01) |
| *A61B 1/00* | (2006.01) |
| *A61B 1/05* | (2006.01) |
| *A61B 1/267* | (2006.01) |
| *A61B 1/06* | (2006.01) |

(52) U.S. Cl.
CPC ....... *A61M 16/0488* (2013.01); *A61B 1/0002* (2013.01); *A61B 1/00052* (2013.01); *A61B 1/00062* (2013.01); *A61B 1/00066* (2013.01); *A61B 1/00103* (2013.01); *A61B 1/00105* (2013.01); *A61B 1/05* (2013.01); *A61B 1/267* (2013.01); *A61B 1/00032* (2013.01); *A61B 1/00059* (2013.01); *A61B 1/0676* (2013.01); *A61B 2560/028* (2013.01); *A61B 2560/0285* (2013.01)

(58) Field of Classification Search
CPC .............. A61B 1/0002; A61B 1/00032; A61B 1/00059; A61B 1/00062; A61B 1/00066; A61B 1/00103; A61B 1/00105; A61B 1/05; A61B 1/267; A61B 2560/028; A61B 2560/0285; A61M 16/0488

See application file for complete search history.

(56) References Cited

U.S. PATENT DOCUMENTS

| | | | | |
|---|---|---|---|---|
| 4,930,495 A | * | 6/1990 | Upsher | A61B 1/267 600/193 |
| 5,702,351 A | * | 12/1997 | Bar-Or | A61B 1/0676 600/185 |
| 5,879,304 A | * | 3/1999 | Shuchman | A61B 1/00103 600/193 |
| 8,075,480 B2 | * | 12/2011 | Nielsen | A61B 1/00062 600/185 |

(Continued)

*Primary Examiner* — Larry E Waggle, Jr.
(74) *Attorney, Agent, or Firm* — Katten Muchin Rosenman LLP

(57) ABSTRACT

An intubation device for intubating a patient includes a handle for holding the intubation device by a user, a single-use intubation blade that includes a retainer clip and a mounting lug held fixedly to the intubation blade by the retainer clip, a ratchet collar that is rotatably connected to the handle. The ratchet collar is rotatable with respect to the intubation blade in a first travel direction to mount the intubation blade to the handle and in a second travel direction to dismount the intubation blade from the handle. The intubation device also includes a disabling mechanism for preventing re-use of the intubation. The disabling mechanism includes a break-away section of the retainer clip, and gear teeth that have a first gear tooth surface. When the ratchet collar is rotated the first gear tooth surface breaks the break-away section dislocating the mounting lug.

14 Claims, 9 Drawing Sheets

(56) References Cited

U.S. PATENT DOCUMENTS

2007/0106121 A1* 5/2007 Yokota ............... A61B 1/00052
 600/188
2010/0261967 A1* 10/2010 Pacey ................ A61B 1/00103
 600/186

* cited by examiner

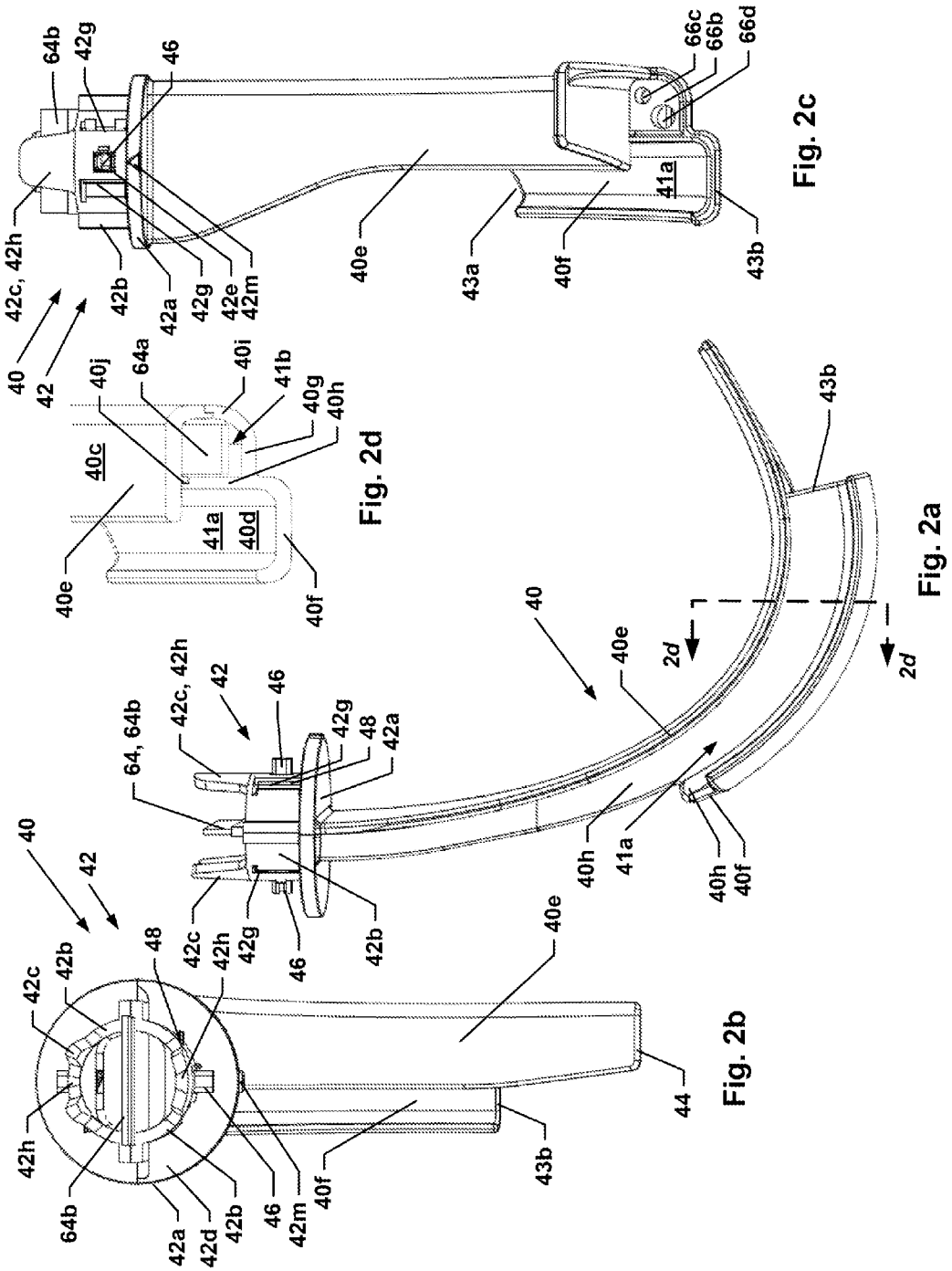

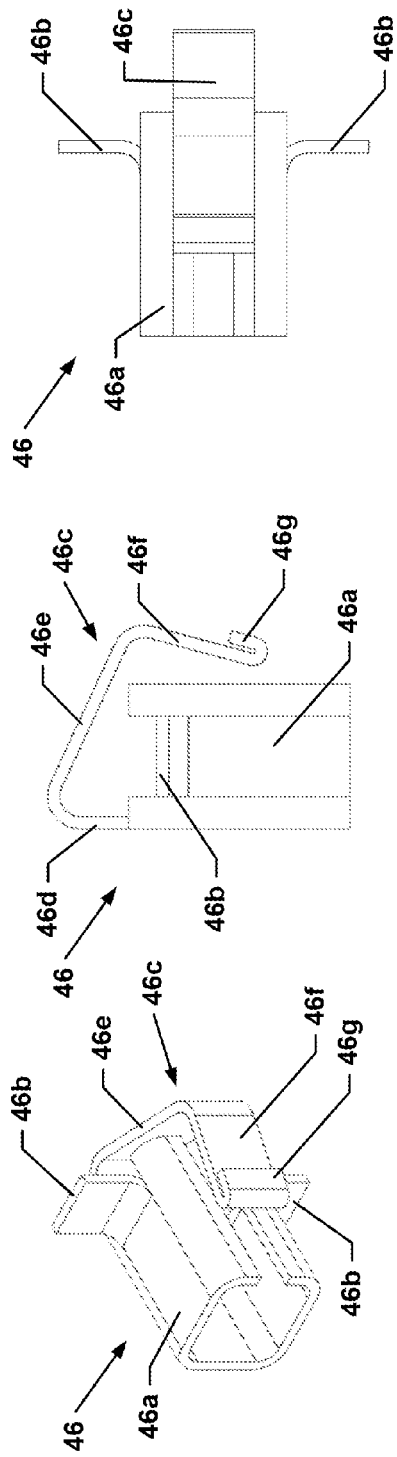
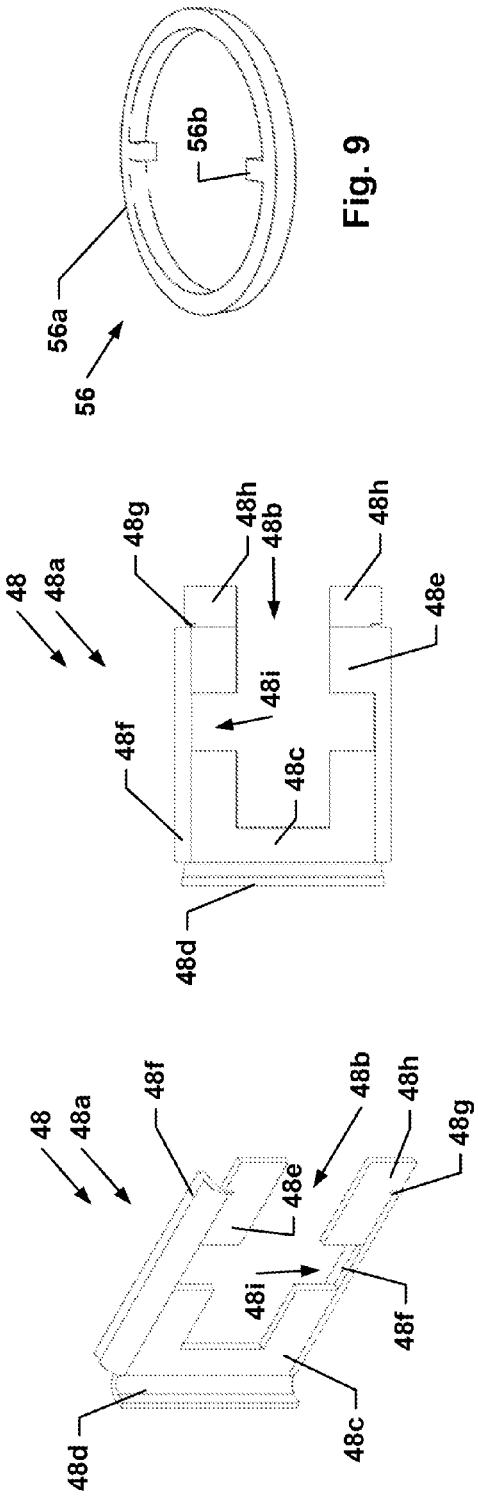

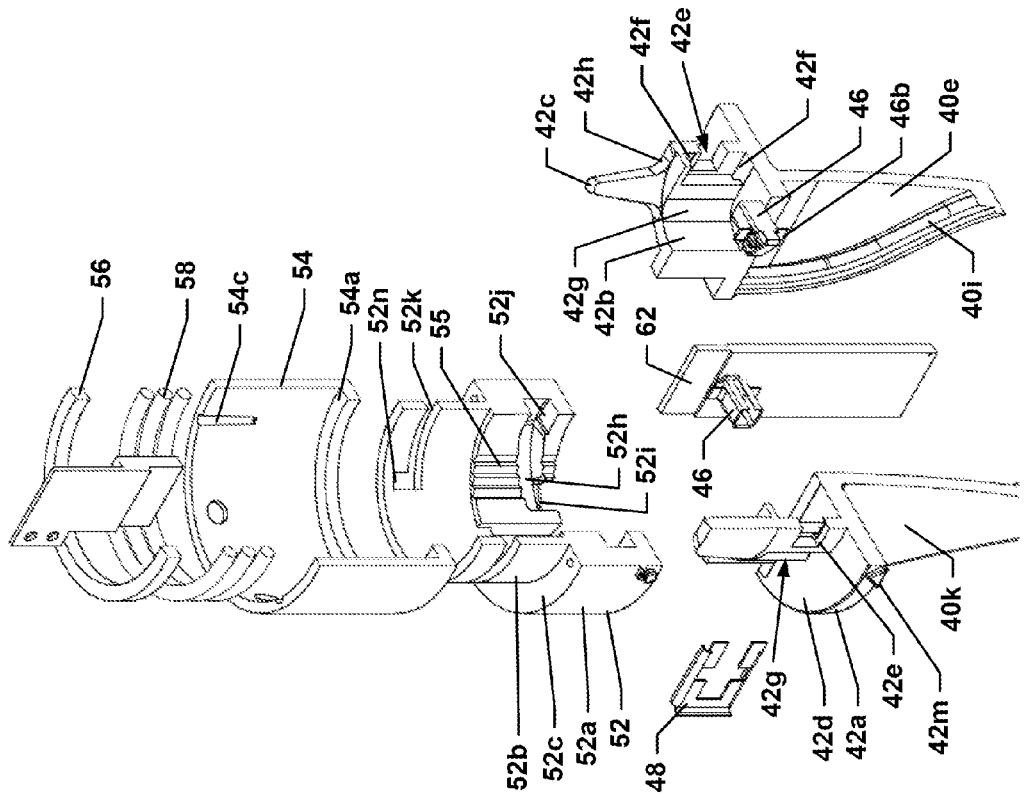
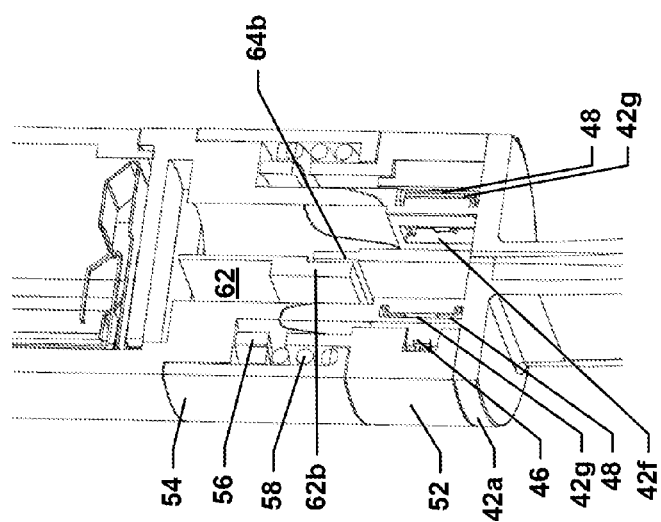

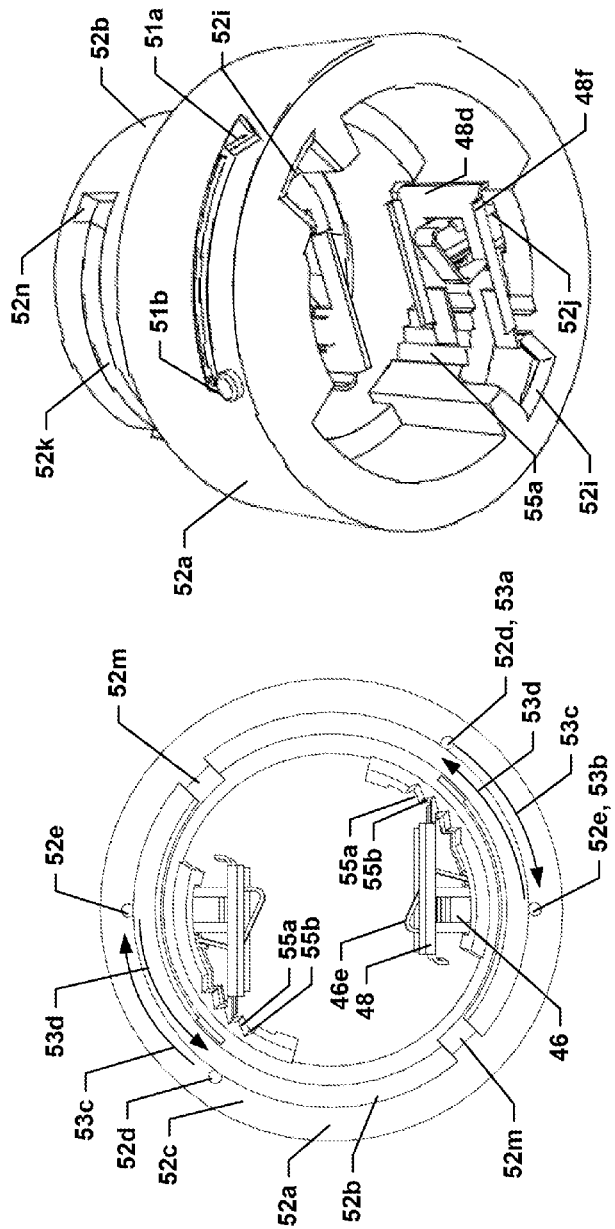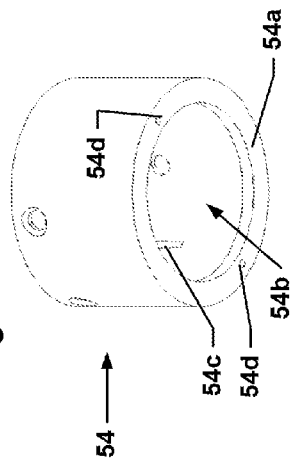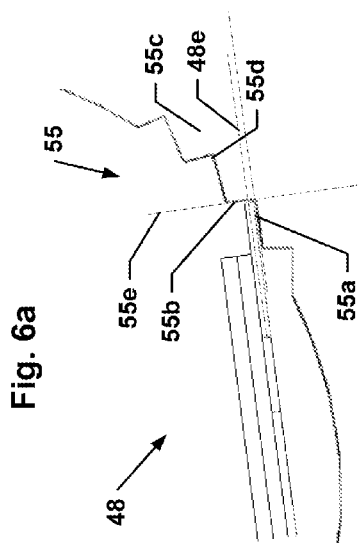

INTUBATION DEVICE

BACKGROUND OF THE INVENTION

1. Field of the Invention

The present invention relates to a device for intubating a patient. Specifically, the invention relates to an intubation device that includes a disposable, single-use intubation blade that includes a portion of an imaging system.

2. Description of the Related Art

Intubation is a medical procedure in which an endotracheal tube is positioned into the trachea, effectively bypassing the mouth, nose, and throat, to provide oxygen directly to the lungs. Intubation is a common procedure performed on any person who cannot manage their own airway. In a hospital setting, this includes people receiving general anesthetic in preparation of surgery, but also includes many emergency situations, where injury and trauma impairs one's airway. Although intubations are performed routinely, complications due to improper or difficult intubations are common.

The insertion of an endotracheal tube is often accomplished using a laryngoscope, but using a laryngoscope requires skill and proper training. The laryngoscope is inserted into the mouth to push away the tongue and lift the epiglottis so that a view of the glottis (space between the vocal cords) is possible. The goal is then to feed the endotracheal tube into the airway and the trachea instead of the esophagus (which is located directly behind the trachea), and then to maintain such placement during patient transport or until the endotracheal tube is removed. If the endotracheal tube is mistakenly placed in the esophagus the mistake can be fatal or lead to brain injury and permanent disability. Statistically, about 8% of all intubations are difficult, which leads to an increased chance of improper intubation.

The problem is that even when a patient's mouth is open, even using a laryngoscope, the vocal chords are not visible, and by feeding the endotracheal tube into the airway, even visual inspection of the glottis becomes blocked. Even if properly placed, a problem may still occur when proper placement of the endotracheal tube is re-checked following placement for example, when patients are transported by ambulance after the patient has been intubated by emergency medical services, where the movement might have dislodged, or partially dislodged the ET.

There are generally three types of instruments that have been utilized to provide video assisted tracheal intubation. The first is the endotracheal tube itself, the second is the laryngoscope blade, and the third is an intubation stylet, i.e. a device which is slid through the center of the endotracheal tube and aids in the insertion of the endotracheal tube into the airway. In each case, an image is transmitted, usually via fiber optic material or the like, from the tip of the instrument to a display that is visible to the doctor during use of the instrument.

With respect to the first two types of instruments, namely the endotracheal tube and the laryngoscope blade, these generally tend to be modifications of the regularly utilized instruments. Specifically, some form of ultra-thin fiber optic is integrated into the instrument which feeds to a display monitor at the end of the instrument or remote of the instrument. Such video-intuboscopy and video laryngoscopy have generally been utilized in hospital settings where extensive monitor equipment is available. Such devices have provided limited, if any, assistance to first responders such as EMS personnel. The video-optical intubation stylet that has been suggested also uses optical fibers for image transmission from the stylet tip to the video camera monitors. However, these also require remote imaging and provide difficult video monitoring, especially in emergency response conditions.

It has also been recently suggested to use video electronics, such as a miniature electric camera which is incorporated in the distal end of the endotracheal tube itself or the stylet. However, no practical implementation of such device has been suggested and no suitable display mechanism has been provided to facilitate usage by emergency responding personnel. Furthermore, most of these devices that have been suggested provide complex structure with inadequate monitoring for the convenience of the medical personnel utilizing such instruments.

SUMMARY OF THE INVENTION

These and other objectives are met by the present invention.

In accordance with one or more embodiments of the present invention, an intubation device for intubating a patient includes a handle for holding the intubation device by a user; a single-use intubation blade, the intubation blade having a retainer clip and a mounting lug held fixedly to the intubation blade by the retainer clip; a ratchet collar rotatably connected to the handle, the ratchet collar rotatable with respect to the intubation blade in a first travel direction to mount the intubation blade to the handle and in a second travel direction to dismount the intubation blade from the handle; a disabling mechanism for preventing re-use of the intubation, the disabling mechanism having a break-away section of the retainer clip, and a plurality of gear teeth, each gear tooth having a first gear tooth surface disposed substantially perpendicularly to a plane having the break-away section. When the ratchet collar is rotated to dismount the intubation blade from the handle, the first gear tooth surface breaks the break-away section dislocating the mounting lug. The handle may also have a first mating portion and the intubation blade may also have a second mating portion. The first mating portion mates with the second mating portion and rotationally locks the handle and the intubation blade.

The ratchet collar includes a mounting channel for directing the mounting lug in the first travel direction and in the second travel direction; an entrance to the mounting channel, the entrance disposed at a bottom surface of the ratchet collar for receiving the mounting lug; and a seating notch at an end of the mounting channel, the seating notch for seating the mounting lug.

The intubation device may also have a biasing assembly that has a biasing collar, a spring, and a spring retainer. The biasing assembly applies a force to seat the mounting lug in the seating notch.

In accordance with one or more embodiments of the present invention, the intubation device may have a biasing assembly that includes or consists of a biasing collar, a spring, and a spring retainer. The ratchet collar includes a retention seating notch at an upper end of the ratchet collar for seating a portion of the spring retainer. When the biasing collar includes a support edge for supporting the spring, the spring is sandwiched between the spring retainer and the support edge.

In accordance with one or more embodiments of the present invention, the intubation device an imaging assembly, the imaging assembly having a lens for acquiring an optical image of a portion of the patient, an imaging unit for acquiring an electronic image of the portion of the patient from the optical image, a display for displaying the electronic image to the user. The lens is preferably disposed near a distal end of the intubation blade. That end is inserted into the patient.

The imaging assembly may have a conduit lead line and a first connector disposed on the intubation blade and a computing unit disposed in the handle. The conduit lead line is connected at one end to the lens and a second end to the first connector. The computing unit may include the imaging unit and a second connector. The second connector is operatively connected with the first connector to transmit the optical images from the lens to the imaging unit.

The intubation device may include for each gear tooth comprises a second gear tooth surface, the second gear tooth surface being substantially parallel to the plane having the break-away section.

In accordance with one or more embodiments of the present invention, an intubation device for performing an intubation on a patient includes a handle for holding the intubation device during the intubation; a collar fixedly joined to the handle; a disposable intubation blade having a break-away section; and a ratchet collar rotatably joined to the collar. The ratchet collar a plurality of gear teeth, each gear tooth having a first gear tooth surface. The ratchet collar is rotatable with respect to the intubation blade to mount the intubation blade in the handle to perform the intubation and the ratchet collar is rotatable with respect to the intubation blade. When the ratchet collar is rotated to dismount the intubation blade from the handle, the first gear tooth surface breaks the break-away section and permitting dismounting of the intubation blade from the handle.

BRIEF SUMMARY OF THE DRAWINGS

FIG. 1b is a rear perspective view of the intubation device of FIG. 1a.

FIG. 1c is an exploded front perspective view of the intubation device of FIG. 1a.

FIG. 1d is an exploded rear perspective view of the intubation device of FIG. 1a.

FIG. 2a is a side view of an intubation blade in accordance with one or more embodiments of the present invention.

FIG. 2b is a top view of the intubation blade of FIG. 2a.

FIG. 2c is a front view of the intubation blade of FIG. 2a.

FIG. 2d is a cross-sectional view of the intubation blade of FIG. 2a.

FIG. 3a is a perspective view of a mounting lug in accordance with one or more embodiments of the present invention.

FIG. 3b is a top view of the mounting lug of FIG. 3a.

FIG. 3c is a right-side view of the mounting lug of FIG. 3a.

FIG. 4a is a perspective view of a retainer clip in accordance with one or more embodiments of the present invention.

FIG. 4b is a front view of the retainer clip of FIG. 4a.

FIG. 5a is a cross-section view of a connector assembly and a proximal end of the intubation blade joined together in accordance with one or more embodiments of the present invention.

FIG. 5b is an exploded cross-sectional view of a connector assembly and a proximal end of the intubation blade joined together in accordance with one or more embodiments of the present invention.

FIG. 6a is a top view of a ratchet collar, a mounting lug, and a retainer clip in accordance with one or more embodiments of the present invention.

FIG. 6b is a bottom perspective view of FIG. 6a.

FIG. 7 is schematic of the gear teeth and the retainer clip in accordance with one or more embodiments of the present invention.

FIG. 8 is a bottom perspective view of a biasing collar in accordance with one or more embodiments of the present invention.

FIG. 9 is a perspective view of a spring retainer in accordance with one or more embodiments of the present invention.

FIG. 10b is a front view of the lug and the retainer clip of FIG. 10a.

DETAILED DESCRIPTION OF THE INVENTION

Figure 1B:
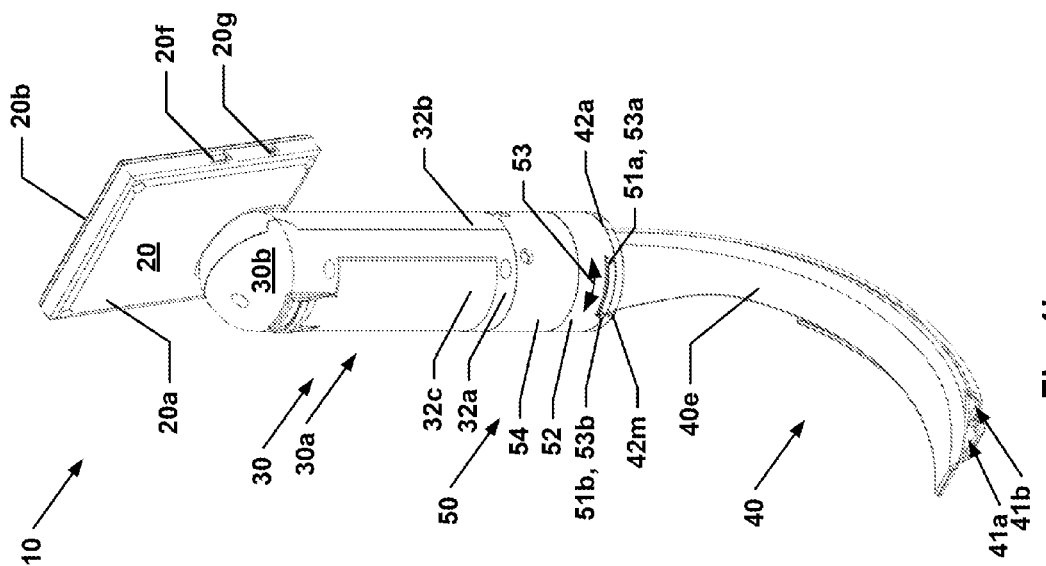

Reference will now be made in detail to several views of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, left, right, up, down, over, above, below, beneath, rear, and front may be used with respect to the drawings. These and similar directional terms should not be construed to limit the scope of the invention in any manner. The words "connect," "couple," and similar terms with their inflectional morphemes do not necessarily denote direct and immediate connections, but also include connections through intermediate elements or devices.

Figure 1A:
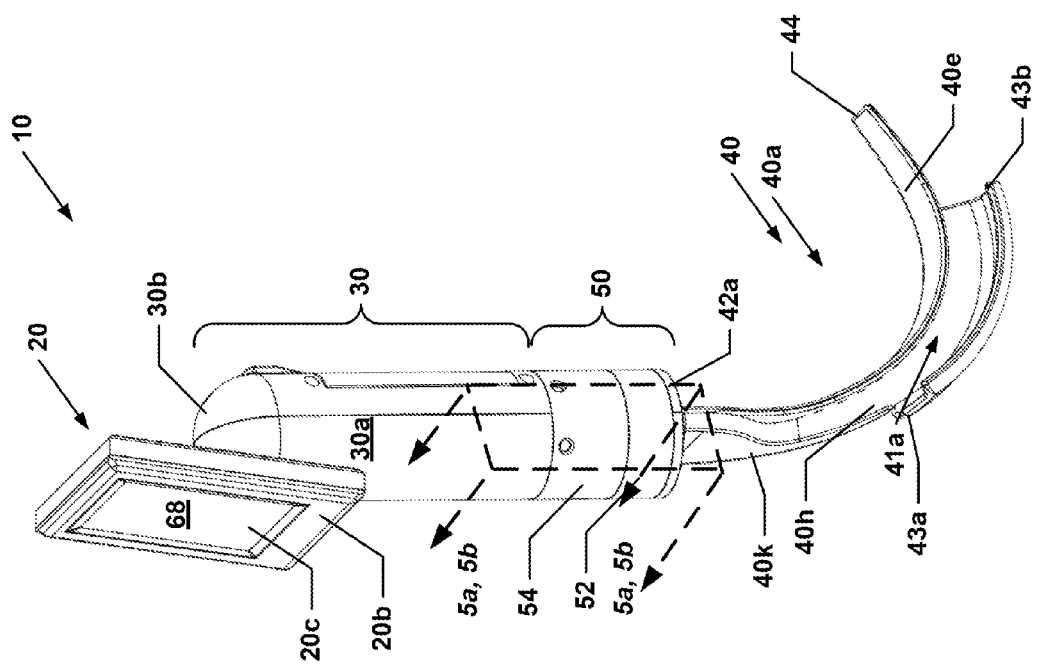
FIG. 1a is front perspective view of an intubation device in accordance with one or more embodiments of the present invention.
Figure 1C:
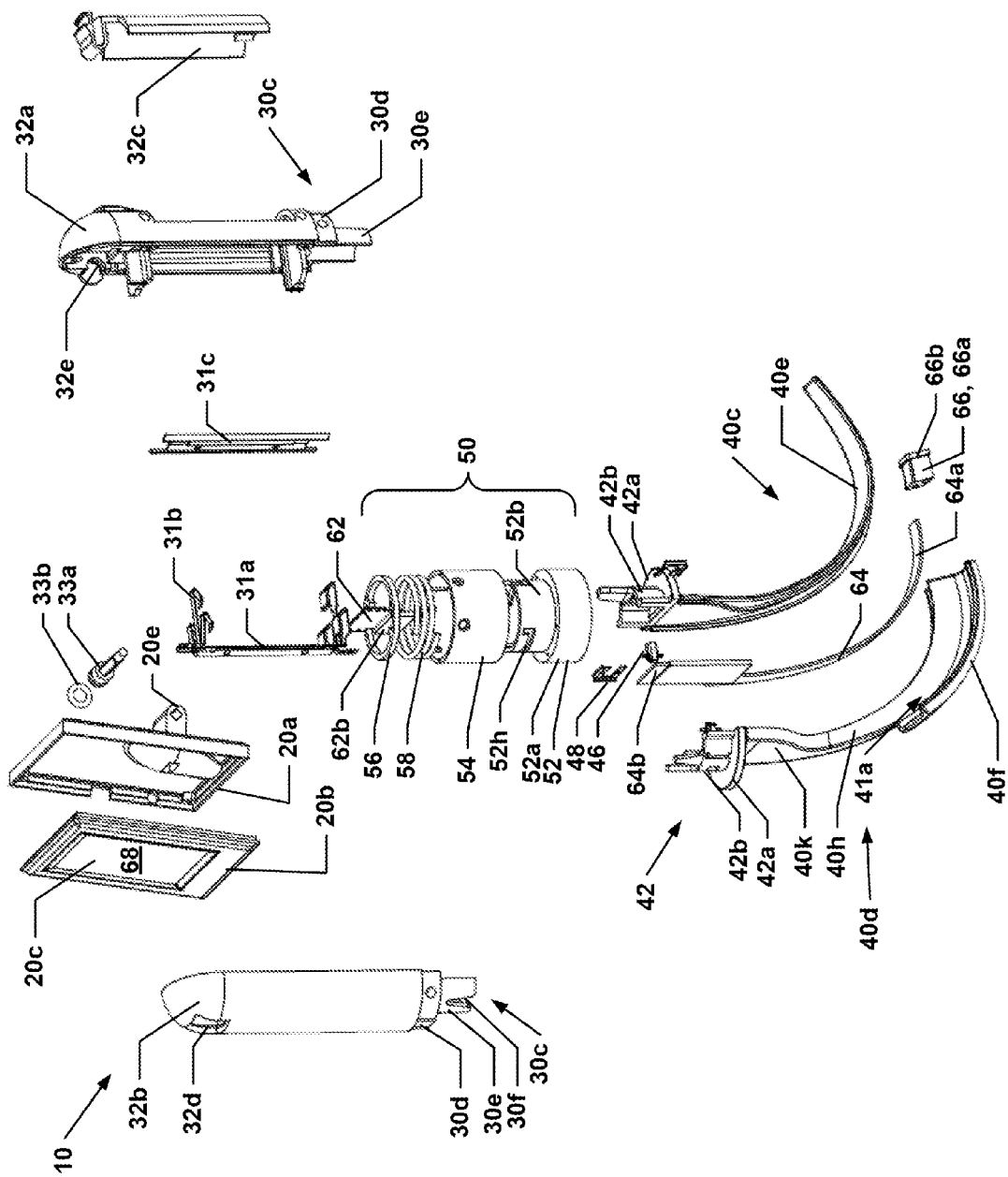
Figure 1D:
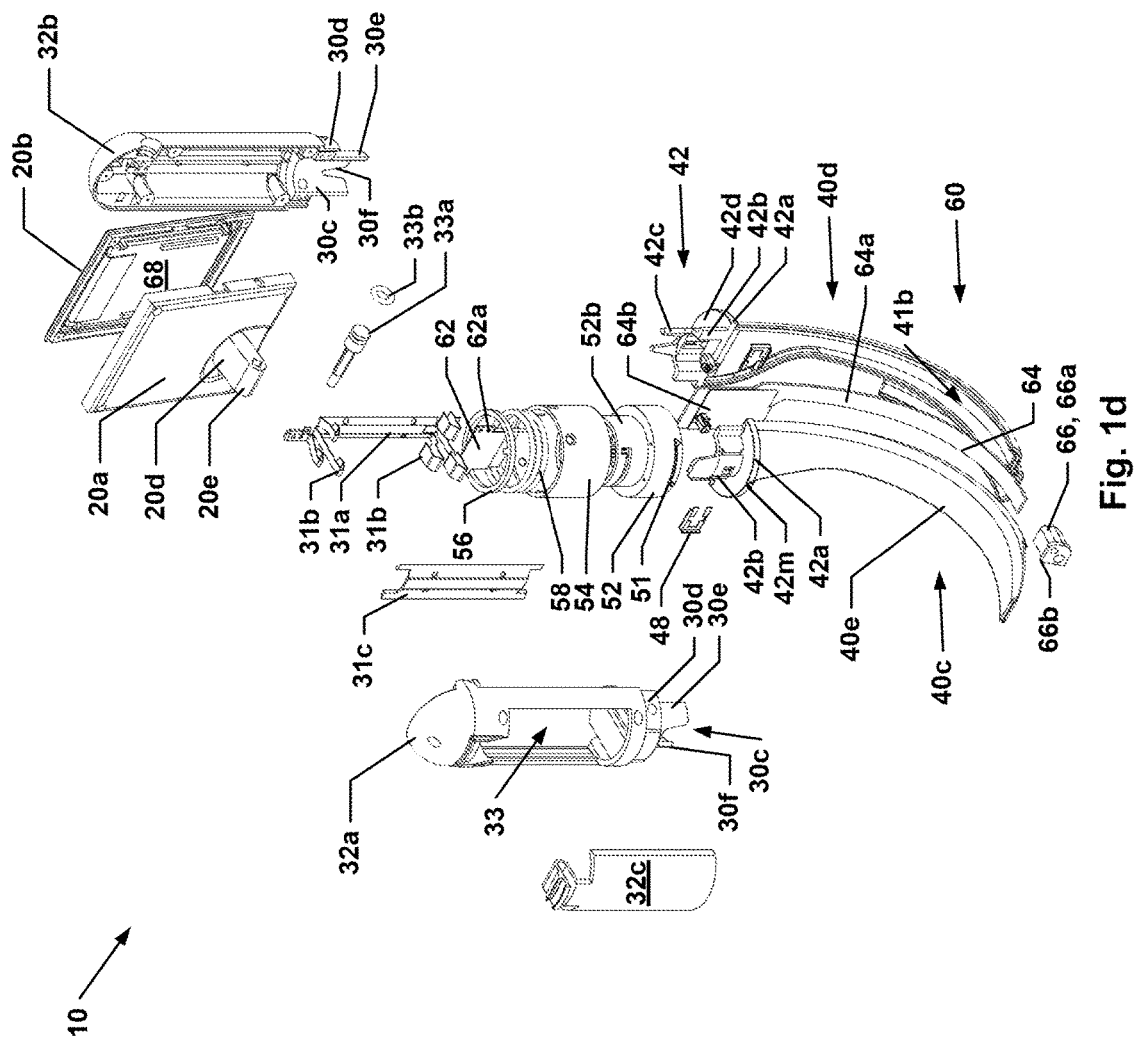

FIG. 1a is front perspective view of an intubation device in accordance with one or more embodiments of the present invention. FIG. 1b is a rear perspective view of the intubation device of FIG. 1a. FIG. 1c is an exploded front perspective view of the intubation device of FIG. 1a. FIG. 1d is an exploded rear perspective view of the intubation device of FIG. 1a.

Therein, intubation device 10 is an orotracheal intubation device for maintaining an open airway of a patient or delivering one or more drugs to a patient through the trachea. Typically, intubation device 10 is used for facilitating the ventilation of the patient's lungs. However, other medically necessary uses of intubation device 10 are also possible, such as delivering drugs into the stomach of a patient. Intubation device 10 may also be adapted for veterinary use.

Intubation device 10 comprises a display housing 20 having a display screen for displaying images and/or video, a handle 30 for holding the intubation device, a disposable, single-use, i.e., non-reuse, replaceable intubation blade 40, a connector assembly 50 for securely connecting, i.e., "mounting," the intubation blade to the handle to perform an intubation and a disabling mechanism for preventing re-use of the intubation blade, and an imaging assembly 60 for acquiring images and/or video of the intubation performed or attempted to be performed with the intubation device. The disabling mechanism comprises a plurality of parts disposed on at least the intubation blade and the connector assembly.

Display housing 20 may be any suitable device and holds a display for visual and/or touch by a user of the intubation device. Therein, display housing 20 preferably comprises a housing 20a and a frame 20b that cooperates with housing 20a to securely sandwich the display. Housing 20a and frame 20b may be secured to each other by snap-fit, screws, or other mounting methods. Frame 20b comprises an opening 20c that permits visual and/or touch access to a screen of display.

Housing 20a comprises a support extension 20d and a first hinge portion 20e at a distal end of the support extension. Support extension 20d may be separately joined to housing 20a, but preferably is formed as a portion of the housing.

One or more openings 20f for one or more respective data ports may be formed through a portion of housing 20a and/or frame 20b. The one or more data ports preferably provide connectivity between devices external to intubation device 10 and data storage media and/or a computing unit internal to intubation device 10. At least one data port preferably is a universal serial bus port (USB) of any type, but may also be an IEEE 1394 (FireWire) or any other suitable data port that provides data connectivity between intubation device 10 and an external device. The externals device may be a surgical suite or a computer and the one or more data ports are used to transfer and save images and/or video of the intubation performed or attempted to be performed by intubation device 10. One or more openings 20g for one or more functional physical controls may be formed through a portion of housing 20a and/or frame 20b.

Handle 30 preferably has an elongated body 30a for grasping by a user, a rounded top 30b to avoid injury of the user, and an extended end 30c for receiving a portion of connector assembly 50. Therein, handle 30 comprises one or more handle housing portions 32 that define an inner space of the handle. Preferably, there are two handle housing portions, i.e., housing portions 32a and 32b, so that the two portions may sandwich portions of the imaging assembly. The handle housing portions may be joined to each other by glue, snap-fit, screw mounting, or any other means.

One or more connectors 31a having flexible ends 31b for connecting to terminals of one or more power sources, such as one or more batteries, are disposed in inner space 33. A panel 31c secures connectors 31a to housing portion 32b. A user removable panel 32c is removable by a user from housing portion 32a to provide access to interior space 33 in order to, for example, replace the one or more power sources.

Each end of the housing portions comprises a portion of the extended end 30c. Extended end 30c has a first extended wall 30d and a second extended wall 30e. Extended walls 30d and 30e may be recessed from an outer surface of elongated body 30a to better receive a portion of connector assembly 50. The extended walls may be also stepped with respect to each other. Thus, for example, extended wall 30e is further inward from the outer surface than extended wall 30d. However, the extended walls may omit the recess and/or not be stepped with respect to each other.

Each of extended walls 30d and 30e may be disposed on one or more of the housing portions. However, some of the housing portions may not comprise either extended wall or may not comprise both extended walls. When a housing portion comprises a portion of extended wall 30e, that portion of extended wall 30e may have an upper mating portion 30f for mating with a lower mating portion disposed in an end of the intubation blade to rotationally lock the handle and the intubation blade together.

Upper mating portion 30f may be an indent or an extension and more than one upper mating portion 30f is preferred on the entirety of extended wall 30e. By using a plurality of upper mating portions 30f that mate with a plurality of lower mating portions, the likelihood of positive seating of the intubation blade in the handle is increased. A smooth shaped indent or extension, as illustrated, for example, in the shape of a sinusoid is preferred for the upper and lower mating portions since it provides smooth seating. However, upper mating portion 30f may have snap fit or locking engagement for mating with the lower mating portion or any other suitable kind of mating.

At least one housing portion, preferably housing portion 32b, comprises an opening 32d for receiving a portion of support extension 20e. A second hinge portion 32e is disposed on an interior of housing portion 32a and receives first hinge portion 20f. A hinge pin 33a is then inserted through openings in each of the first and second hinge portions to rotatably link the display housing and the handle together. This permits display housing 20 to rotate with respect to the handle for convenience of the user. Therein, opening 32d is preferably sized to permit display housing 20 to rotate between 30-90 degrees relative to the handle. A seal 33b may be disposed to prevent intrusion of water of bodily fluids into the interior of handle 30.

FIG. 2a is a side view of an intubation blade in accordance with one or more embodiments of the present invention. FIG. 2b is a top view of the intubation blade of FIG. 2a. FIG. 2c is a front view of the intubation blade of FIG. 2a. FIG. 2d is a cross-sectional view of the intubation blade of FIG. 2a.

Intubation blade 40 comprises an elongated body 40a in the shape of any standard or non-standard intubation blade known in the art. Intubation blade 40 comprises a first longitudinal blade portion 40c, a second longitudinal portion 40d, a proximal end 42 that is removably secured to handle 30 and a distal end 44 that is inserted into the airway of the patient. The two longitudinal blade portions are joined together to form the intubation blade by being snap fit, glued, sonically welded, or by some other means joined together. Each of the proximal and distal ends may be disposed at least partially on each of the longitudinal blade portions 40c and 40d.

The first longitudinal blade portion comprises a first intubation wall 40e that extends from the proximal portion to the distal end. Intubation wall 40e comprises a rounded edge at a side of the wall and a narrowed distal end, both of which serve to prevent injury to the patient. Intubation wall 40e may be a flat wall or a generally L-shape wall, as shown.

The second longitudinal blade portion comprises a second intubation wall 40f and a third intubation wall 40g. Walls 40f and 40g may be flat walls, but preferably wall 40f comprises a generally U-shaped wall starting at a generally first medial location 43a and extending to a second medial location 43b on the intubation blade. A channel 41a is formed between walls 40e and 40f through which medical devices are advanced into the trachea of the patient.

Wall 40g preferably has a generally U-shaped wall sharing a medial wall 40h with wall 40f and having an outside wall 40i that meets wall 40e to form a closed channel 41b. Channel 41b houses a portion of the imaging assembly and extends from proximal end 42 to a third medial location 43c, which is spaced from distal end 44 but is closer to distal end 44 than medial location 43b. A further wall 40k is joined substantially perpendicularly to medial wall 40h, which extends from proximal end 42 to distal end 44.

A protruding medial wall 40j that is substantially perpendicular to wall 40e may be overlapped to a portion of wall 40h to form a structurally advantageous joint between the first and the second longitudinal blade portions.

Proximal end 42 comprises a base 42a, one or more uprights walls 42b, and one or more extended wall portions 42c. Base 42a preferably comprises a plane and extends transversely to walls 40e, 40k. Upright walls 42b are recessed from a peripheral edge 42d of the base so that a portion of the connector assembly is disposed over an outer perimeter of the upright walls.

Preferably, at least one upright wall comprises an opening 42e for receiving a mounting lug 46. One or more notches 42f are provided in a rear of wall 42b for receiving one or more portions of the mounting lug and preventing the mounting lug to pass entirely through opening 42e. A pair of slots 42g is provided through wall 42b for receiving a retainer clip 48 for securing the mounting lug. Therein, slots 42g are oriented along an axis that is substantially perpendicular to an axis passing through opening 42e.

One or more lower mating portions 42h are disposed on at least some but preferably all extended wall portions 42c to mate with the upper mating portions and seat the intubation blade in the handle. Therein, a smooth shaped indent or extension, as illustrated, for example, in the shape of a sinusoid is preferred for the upper and lower mating portions since it provides smooth seating. However, lower mating portion 42h may have snap fit or locking engagement for mating with the upper mating portion or any other suitable kind of mating.

FIG. 3a is a perspective view of a mounting lug in accordance with one or more embodiments of the present invention. FIG. 3b is a top view of the mounting lug of FIG. 3a. FIG. 3c is a right-side view of the mounting lug of FIG. 3a.

Mounting lug 46 preferably comprises a tubular-shaped body 46a having one or more retaining tangs 46b and an end spring 46c. Tangs 46b are received in respective notches 42f. End spring 46c comprises an extension 46d, a first angled portion 46e and a second angled portion 46f, and an anchor 46g. Extension 46d and the first and second angled portions permit the end spring to be biased, while the anchor retains the lug in an opening by being pushed against the wall that surrounds the opening.

FIG. 4a is a perspective view of a retainer clip in accordance with one or more embodiments of the present invention. FIG. 4b is a front view of the retainer clip of FIG. 4a.

Retainer clip 48 comprises a generally U-shaped body 48a having a central opening 48b, an end section 48c disposed with an end catch 48d, a pair of longitudinal sections 48e each, and a pair of curved rails 48f. Central opening 48b is sized to fit without play over tubular-shaped body 46a of the lug. End catch 48d prevents the retainer clip from passing through slot 42g. A pair of notches 48g is provided in the longitudinal sections 48e at the ends of rails 48f. The notches weaken the longitudinal sections causing the end portions 48h of the longitudinal sections to break off when the intubation blade is removed, i.e., portions 48h are break-away sections. In accordance with one or more embodiments of the present invention, notches 48g permit a portion of the retainer to bend. When rails 48f are bent, notches 48g are necessary so the retainer clip can continue to 48h, which is the portion that ratchets when the blade is attached, and then is used to drive the retainer over by the teeth when the blade is disconnected. A pair of spaces 48i between end section 48c and longitudinal sections 48e is sized to permit tangs 46b to pass.

For reason of economy, both the lug and the retainer clip are preferably made of sheet metal that is stamped and bent to the shape of the lug or retainer clip, respectively. The ratchet collar, biasing collar, spring retainer, and spring for reasons of strength are preferably made of metal. The intubation blade and handle may feature one or more components made of metal, but in general all housing portions of these two are made of medical grade plastic. The imaging assembly is generally made of a mix of materials as is known in the art for electronic components and/or devices.

FIG. 5a is a cross-section view of a connector assembly and a proximal end of the intubation blade joined together in accordance with one or more embodiments of the present invention. FIG. 5b is an exploded cross-sectional view of a connector assembly and a proximal end of the intubation blade joined together in accordance with one or more embodiments of the present invention.

FIG. 6a is a top view of a ratchet collar, a mounting lug, and a retainer clip in accordance with one or more embodiments of the present invention. FIG. 6b is a bottom perspective view of FIG. 6a.

FIG. 7 is schematic of the gear teeth and the retainer clip in accordance with one or more embodiments of the present invention.

FIG. 8 is a bottom perspective view of a biasing collar in accordance with one or more embodiments of the present invention.

FIG. 9 is a perspective view of a spring retainer in accordance with one or more embodiments of the present invention.

Figure 10A:
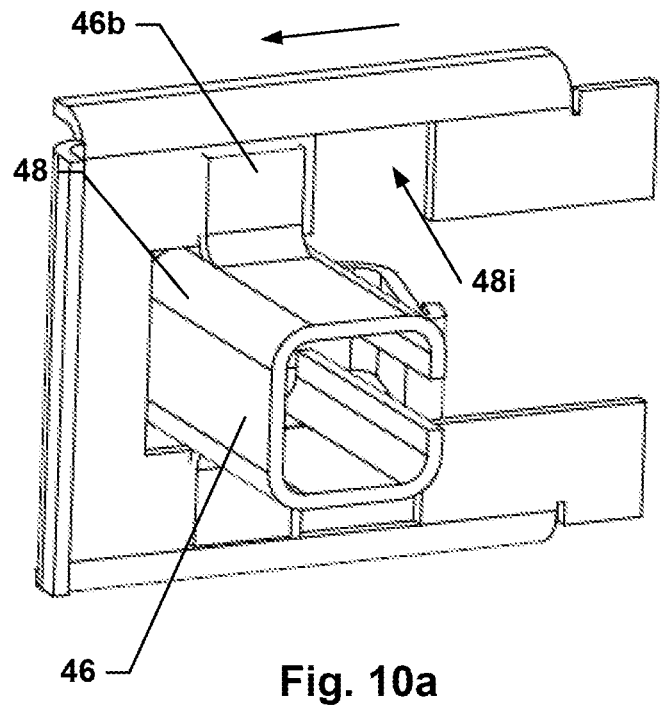
FIG. 10a is an isometric view of a lug and a retainer clip in accordance with one or more embodiments of the present invention.

FIG. 10a is an isometric view of a lug and lug retainer in accordance with one or more embodiments of the present invention.

Figure 10B:
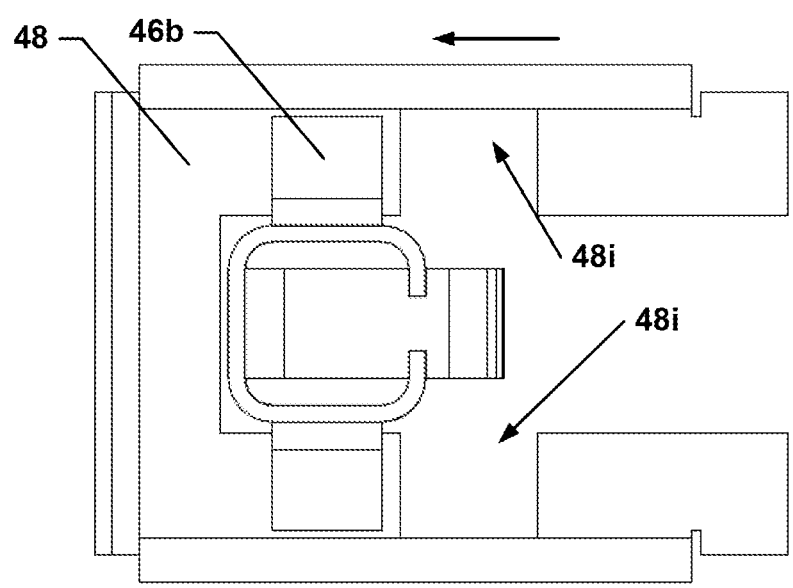

FIG. 10b is a front view of the lug and lug retainer of FIG. 10a.

Connector assembly 50 comprises a ratchet collar 52, a biasing collar 54, a spring retainer 56, and a spring 58. Ratchet collar 52 comprises a generally stepped shape having a throughbore. The ratchet collar comprises a lower portion 52a having a circumferential wall and open bottom and an upper portion 52b having also a circumferential wall and an open top. The upper portion is recessed from the lower portion, and, thus, the lower portion comprises a shoulder 52c.

One or more raised markers are provided on shoulder 52c, and, as further explained below, provide a touch-sensitive response to biasing collar 54 being turned with respect to ratchet collar. Therein, raised markers are 52d, 52e provided in pairs and correspond to a start point 53a and end point 53b of travel direction 53, i.e., a first travel direction 53c from 53a to 53b when mounting the intubation blade and a second travel direction 53d from 53b to 53a when removing the intubation blade. The start and end points 53a, 53b are visually indicated on indicator 51; therein, position 53a is indicated by marker 51a of indicator 51 and position 53b is indicated by marker 51b of indicator 51. Preferably, indicators 51a and 51b are visually different and/or also tactilely different to a user. The location of the intubation blade is confirmed by an indicator 42m on base 42a of the intubation blade. When the intubation blade is in use, indicator 42m and marker 51b are aligned to show a user that the intubation blade is at position 53b.

Lower portion 52a comprises a plurality of gear teeth 55 on an inner surface of the lower portion. The gear teeth are preferably provided in pairs symmetrically spaced on opposite sides of the inside surface of the ratchet collar and cooperate with end portions 48h which have ends 48e disposed in plane 55c, to form a ratchet in the first travel direction 53c. Specifically, one or more gear teeth include a sliding surface 55a and a stopping surface 55b. Sliding surface 55a is disposed in plane 55d and stopping surface 55b is disposed in plane 55e. Therein, plane 55d is preferably parallel or coincident with plane 55c. Plane 55e is perpendicular to plane 55c and/or plane 55d to prevent the inadvertent movement of the intubation blade relative to the connection assembly.

On an inner surface of the ratchet collar, the lower portion further comprises one or more mounting channels 52h for directing, permitting, and/or moving a respective mounting lug in the first travel direction 53a and the second travel direction 53b. Each mounting channel connects an entrance 52i for receiving a portion of the one or more mounting lug 46 and a seating notch 52j for retaining a portion of mounting lug 46 when the intubation device is in use. The entrance preferably is disposed at the intersection of the inner surface and the bottom surface of the ratchet collar and is sized to receive width 46e that includes the width of the end spring. The channel is angled with respect to the bottom surface of the ratchet collar and also increases in depth relative to the inner surface of the ratchet collar from the entrance to the seating notch.

Upper portion 52b comprises one or more retention channels 52k for advancing the spring retainer. Each channel connects an entrance 52m at a top surface of upper portion 52b and a retainer seating notch 52n that is disposed distal from the ratchet collar; the channel receives an inward extension of the spring retainer in the entrance and advances it and seats the inward extension in retainer seating notch 52n in order to keep the spring compressed.

Biasing collar 54 comprises throughbore, a circumferential wall forming a cylinder, an open top, and an open bottom. A support edge 54a is disposed inwardly at the bottom leaving an opening 54b. Opening 54b is sized to smoothly move over upper portion 52b of the ratchet collar. Support edge 54a may be an inwardly disposed peripheral edge, but may also be one or more inwardly extending tabs spaced from other tabs.

One or more guide slots 54c may be disposed on an inner surface of the biasing collar and receive raised extensions from housing portions 32a, 32b for positive seating. One or more pairs of indents 54d are disposed on the bottom surface of the biasing collar and receive raised markers 52d, 52e.

Spring retainer 56 comprises a substantially circular body 56a in plan view. A one or more inward extensions 56b are disposed in the circular body and are received in entrance 52m, advanced in channel 52k to seating notch 52n where they are seated.

Spring 58 may be any kind of spring, but preferably is a coil wire spring having a substantially circular shape in plan view. The spring is sized to fit smoothly move over upper portion 52b, but inside biasing collar 54. Spring 58 is sandwiched between support 54a and spring retainer 56 and all three form a biasing assembly that biases biasing collar 54 and ratchet collar 52 closer together and consequently biases intubation blade and the handle towards each other to help avoid inadvertent disengagement of the intubation blade with the handle.

In accordance with one embodiment of the present invention, the spring and spring retainer of the biasing collar, i.e., "collar," are not used. Thus, the collar is fixedly joined to the handle and the ratchet collar is rotatably joined to the collar.

Imaging assembly 60 comprises a computing device 62, a conduit 64, a sensor module 66, and a display 68, all of which are operatively connected to the power source.

Computing device 62 is embodied as a printed circuit and one or more central processing units for processing a variety of data, one or more random access memory storages for storing data during processing, one or more non-transitory computing unit media storages (such as a hard drive, a solid state drive, and/or a flash memory) for storing computing unit executable programs and data irrespective of the presence of electric power.

Computing device 62 comprises a plurality of mounting holes 62a through which screws or other mounting devices permit mounting of computing device 62 to the one or more housing portions 32a, 32b. Computing device 62 further comprises a connector 62b, which may be any connector that provides a secure connection to a connector 64b of conduit 64. Conduit 64 preferably comprises a lead line 64a, i.e., a "conduit lead line," and connector 64b. The lead line places connector 64b and sensor module 66 in operative communication. Connector 64b may be any connector that provides a secure connection to connector 62b. Therein, connectors 62b and 64b may be touching or be fully or partially socketed one into the other.

Sensor module 66 may comprise a housing 66a having a front face 66b that is preferably disposed with a peripheral edge about the main body of the housing. A light emitting diode (LED) 66c for s disposed in the housing and illuminates the patient's trachea such that images may be made. Therein, LED 66c is positioned for an efficient use of space to minimize the size of the senor module. The sensor module is disposed in a distal end of channel of channel 41b. Housing 66a preferably fits without play in channel 41b. Front face 66b is sized such that its peripheral edge seals bodily fluids from channel 41b. Therein, the front face may be glued, sonically welded, or permanently or temporarily joined to walls 40e, 40g, 40h, 40i, and/or 40j.

In accordance with one or more embodiments of the present invention, channel 41b is closed from the front face 66b to base 42a.

In accordance with one or more embodiments of the present invention, an imaging unit may be disposed on a printed circuit board (not shown) in the form one or more CCD sensors or CMOS modules (not shown) or the like that functions as a camera component. However, preferably, computing device 62 further comprises an imaging unit having one or more CCD sensors or CMOS modules or the like that function as one or more respective camera components. Preferably conduit 64b a fiber-optic cable operatively connecting the via connectors 62d and 64d to a lens 66d disposed at a distal end of sensor module 66. The lens receives an optical image of the patient's trachea during the intubation being made or being attempted.

Computing device 62 is operatively connected display 68 to provide still and/or moving images of the patient's intubated trachea. Display 68 may be any suitable display such as a liquid crystal display, a plasma display, a three-dimensional display, but other types of screens or displays may also be used. Display 68 displays electronic images and/or video acquired and/or processed by the imaging unit during the intubation being made or being attempted.

If the display screen of display 68 is touch sensitive, display 68 also functionally control the imaging assembly through software loaded in the non-transitory memory of the computing unit. Thus, display 68 may control the size of the image and/or video being taken by changing either the optical or digital zoom. One or more images and/or videos related to prior intubations, instructions for use of the intubation device, safety warnings, or any other topic may also be stored in the non-transitory memory of the computing unit. The non-transitory memory may also be accessed through data ports disposed in one or more openings 20*f*.

In accordance with one or more embodiments of the present invention, instead of or in addition to sensor module 66, a camera having an imaging unit may be installed in channel 41*b* or at a distal end of channel 41*b*. Therein, the camera transmits electronic images to computing device 62 via conduit lead line 64*a* and connector 64*b* connected to connector 62*b*. Conduit 64*b* may then be any wire that may be necessary for use.

In use, an intubation blade 40 is provided in a kit or singly and, in any event, is packaged medically sterile. The intubation blade 40 is for a disposable, single-use, i.e., non-reuse, and is replaceable by a new intubation blade after use of the first intubation blade to avoid infection.

Prior to removal of the intubation blade from its packaging, handle 30 and connector assembly 50 are sterilized any intubation blades have been removed from the handle and connector assembly. Display housing 20 may have been removed from handle 30 by removing hinge pin 33*a* and seal 33*b* and disconnecting display 68 operatively from computing device 62. The display housing is then reassembled with respect to the handle and the display is operatively connected to the computing unit.

To mount the new, unused intubation blade, the blade is oriented so that when inserted, i.e., received in the handle, lower mating portion 42*h* of the intubation blade mates with upper mating portion 30*f* of the handle. Therein, it is helpful to have indicator 42*m* of the intubation blade is more adjacent to indicator 51*a*, i.e., "aligned," than with indicator 51*b*. Indicator 51*a* will signal to user that mounting lugs 46 are aligned with entrance 52*i*. If indicator 42*m* is not aligned with indicator 51*a*, before insertion of the fresh, unused intubation blade, although ratchet collar 52 is turned in second travel direction 53*d* relative to biasing collar 54. Since biasing collar 54 is non-rotationally joined to handle 30, turning ratchet collar 52 in second travel direction 53*d* also turns the ratchet collar relative to handle 30. The user can feel when the end of the travel is reached because raised markers 52*d* of the ratchet collar will seat in recesses 54*d* of the biasing collar.

The new, unused intubation blade is then inserted in a longitudinal direction relative to an axis of the handle into the ratcheting collar so that lug 46 passes through entrance 52*i*. Indicator 42*m* and indicator 51*a* should then be adjacent to each other with certain parts of the indicator, such as the peak of triangles, be substantially aligned with each other.

The new, unused intubation blade is then rotated in first travel direction 53*c*. This causes the lug to travel in channel 52*h*. As the lug travels in channel 52*h*, ends 48*e* also advance in first travel direction 53*c*. Since channel 52*h* is sloped towards the handle, the movement of proximal end 42 relative to the connection assembly causes spring 58 to compress and effect a biasing force away from handle 30 towards intubation blade 40.

Because the gear teeth are shaped to function as a ratchet with ends 48*e*, the ends prevent lug from inadvertently moving in second travel direction 53*d*. When lug 46 has reached the end of travel channel 52*h*, it becomes seated in seating notch 52*j*. Since the seating notch is slightly depressed from channel 52*h*, this gives the user a tactile response that the end of the channel has been reached and the lug has been seated in seating notch 52*j*.

Moreover, a separate tactile indication is given to the when the end of the travel is reached because raised markers 52*e* of the ratchet collar will seat in recesses 54*d* of the biasing collar. A third way the ratchet collar will indicate to a user that the end of the channel has been reached and the one or more lugs have been seated in seating notch 52*j* is when indicator 42*m* is aligned with indicator 51*b*.

Thus, the new intubation blade is then securely connected, i.e., mounted, to the handle and the user can perform an intubation with intubation device 10.

Singly or in combination seating 52*j*, ends 48*e*, and gear teeth 55 prevent inadvertent removal of intubation blade 40 from the connection assembly. A stylet, a medical device, and/or an analysis device may then be advanced via channel 41*a* into the patient's trachea or oragastric passageways.

To remove the intubation blade after use, i.e., "dismount," the user grasps connector assembly 50 and either or both the intubation blade and the handle. The user then forcefully turns or twists, i.e., "rotates," the connector assembly along second travel path 53*d* relative to the intubation blade and/or the handle. Since the intubation blade and the handle are mated together through the lower mating portion and the upper mating portion, twisting the connector blade relative to either is the same as twisting it relative to the other. "Forcefully" is defined herein as strong enough to unseat the lugs from seating notch and break or bend ends 48*e* at notches 48*g* using gear teeth 55, specifically surface 55*b* in plane 55*e*. This permits the lugs to move out of opening 42*e* and fall in the space behind wall 42*b*. Since the lugs include tangs 46*b*, the lugs are unable to pass through opening 42*e* and, for example, become disposed on peripheral edge 42*d*.

In accordance with one or more embodiments of the present invention, the space behind each wall 42*b* of each housing portion may be sealed to the exterior, by, for example, a wall parallel or substantially parallel to base 42*a*, so that the lug is retained in the space behind wall 42*b* without potentially falling out of the intubation blade and becoming a hazard due to potential biological or infectious contamination. Therein, the disabling mechanism comprises or consists of the retainer clip having ends 48*e* and notches 48*g*, the connector assembly having ratchet collar 52 and gear teeth 55, which in turn has surface 55*b* in a plane 55*e* substantially perpendicular to the plane 55*c* of the ends 48*e*. The disabling mechanism further includes one or more lugs 46, tangs 46*b*, and opening 42*e*. The fall then causes the lugs to be located askew relative to their prior position to prevent the lugs from returning to their original position. Moreover, since the lugs include tangs 46*b*, the lugs are unable to pass through opening 42*e* and, for example, become disposed on peripheral edge 42*d*.

Once the one or more lugs have been dislodged from their respective opening 42*e*, intubation blade 40 can be removed from the ratchet collar by turning the intubation blade in second travel direction 53*d* and the intubation blade is removed from the handle in a reverse of the above longitudinal direction.

FIG. 10*a* is an isometric view of a lug and lug retainer in accordance with one or more embodiments of the present invention. FIG. 10*b* is a front view of the lug and lug retainer of FIG. 10*a*. Therein, end portions 48*h* of retainer clip 48 do not break off during the dismounting, but rather retainer clip 48 is pushed by gear teeth, i.e., surfaces 55*a* or 55*b* (preferably stopping surface 55*b*), relative to slot 42*g* sufficiently so that the one or more tangs 46*b* of lug 46 slide into respective spaces 48*i* as the retainer clip moves (as shown by the arrows in FIGS. 10*a* and 10*b*).

Thus, to remove the intubation blade after use, i.e., "dismount," the user grasps connector assembly 50 and either or both the intubation blade and the handle. The user then forcefully turns or twists, i.e., "rotates," the connector assembly along second travel path 53*d* relative to the intubation blade and/or the handle. "Forcefully" is further defined herein as strong enough to move the retainer clip relative to slot 42*g* and unseat, i.e., dislodge, the one or more lugs from their respecting seating notch. Retainer clip 48 is pushed by gear teeth, i.e., surfaces 55*a* or 55*b* (preferably stopping surface 55*b*), relative to slot 42*g* sufficiently so that tangs 46*b* of lug 46 slide in respective spaces 48*i* and away from the ratchet teeth. This permits the lugs to move out of opening 42*e*, i.e., dislodge and fall, i.e., be injected, in the space behind wall 42*b*. The fall then causes the lugs to be located askew relative to their prior position to prevent the lugs from returning to their original position. Moreover, since the lugs include tangs 46*b*, the lugs are unable to pass through opening 42*e* and, for example, become disposed on peripheral edge 42*d*.

In accordance with one or more embodiments of the present invention, the space behind each wall 42*b* of each housing portion may be sealed to the exterior, by, for example, a wall parallel or substantially parallel to base 42*a* or a wall that has a regular or irregular crowned or indented shape comprising a plane parallel to or substantially parallel to base 42*a*, so that the lug is retained in the space behind wall 42*b* without potentially falling out of the intubation blade and becoming a hazard due to potential biological or infectious contamination. Thus, unless the intubation blade is deliberately broken open, the lug remains inaccessible and the blade in any event is not re-usable.

In accordance with one or more embodiments of the present invention, the disabling mechanism may be incorporated in any other device benefitting from a feature that prevents reuse of a component.

Figure 1E:
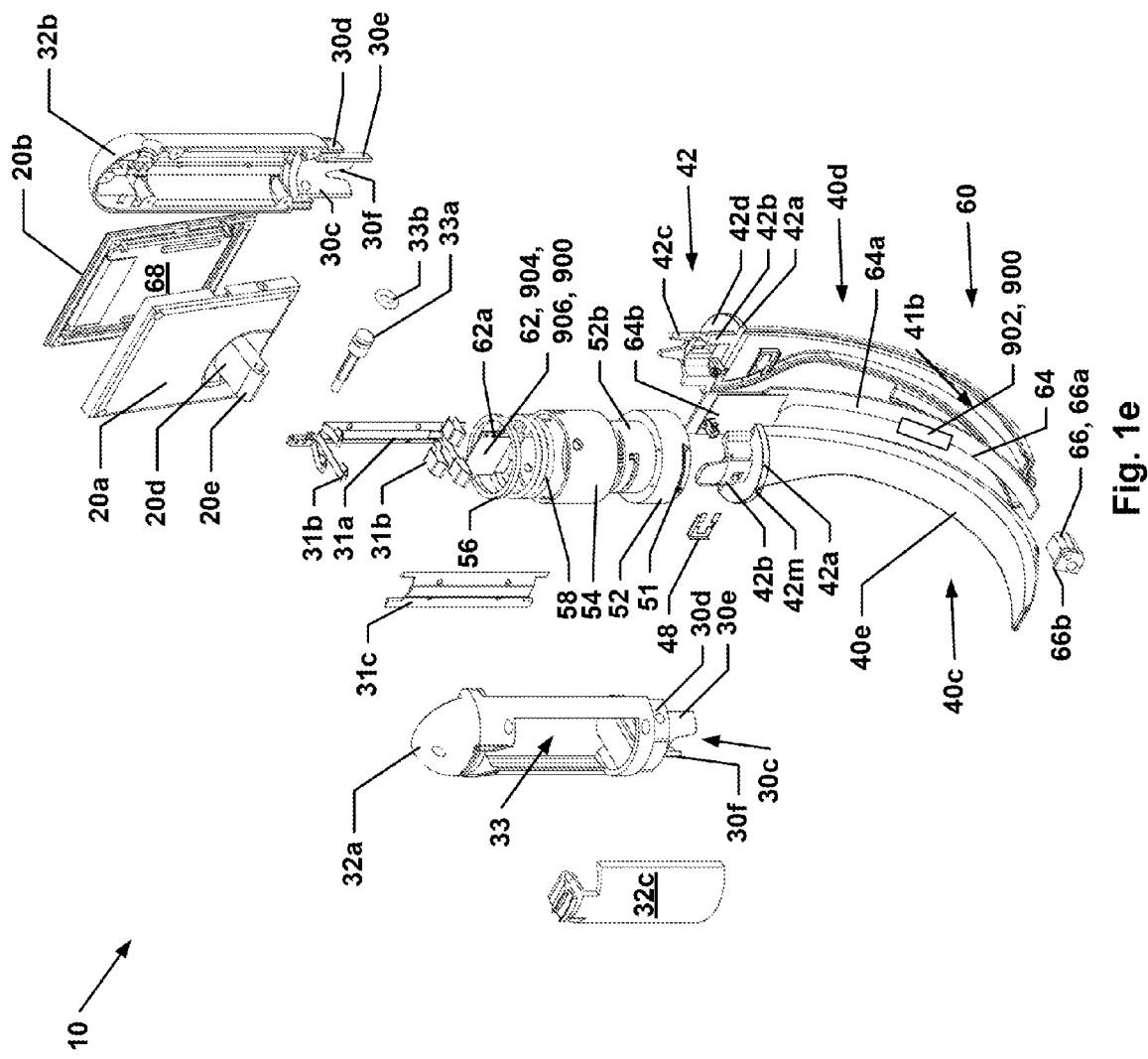
FIG. 1e is an exploded rear perspective view of the intubation device of FIG. 1a further comprising an electronic disabling mechanism.

FIG. 1*e* is an exploded rear perspective view of the intubation device of FIG. 1*a* further comprising an electronic disabling mechanism.

In accordance with one or more embodiments of the present invention, the disabling mechanism may be an electronic disabling mechanism instead of or in addition to the mechanical disabling mechanism. In accordance with one or more embodiments of the present invention, the disabling mechanism may consist of only an electronic disabling mechanism or only the mechanical disabling mechanism. Thus, intubation blade 40 cannot be reused to reduce or avoid issues of biological and/or infectious contamination. Advantageously, an electronic disabling mechanism instead of or in addition to the mechanical disabling mechanism does not require an interaction by a user.

The electronic disabling mechanism 900 comprises and/or consists of an usage storage device 902 disposed on or in intubation blade 40, an instruction issuance device 904 is disposed in or on handle 30 and more particularly in computing device 62 as a unit of computing device 62, and an usage interpretation device 906 is disposed in or on handle 30 and more particularly in computing device 62 as a unit of computing device 62.

The usage storage device 902 may be any suitable device, but preferably is configured as a radio frequency identification chip, a flash memory device, solid state memory device or other data storage device and preferably includes all necessary controller devices. Usage storage device 902 may be located at or near proximal end 42 to be operationally accessible to instruction issuance device 904 and/or usage interpretation device 906. Usage storage device 902 may also be associated with imaging assembly 60 and therein preferably with sensor module 66 by being closely located therewith. Usage storage device 902 may be operationally connected to computing device 62 via conduit 64 to be operatively connected to the power source.

Instruction issuance device 904 and/or usage interpretation device 906 may be configured as computing device having a memory having a physical form, such as a solid state device, and a processor for interpreting one or more instructions or sets of instructions. Instruction issuance device 904 and/or usage interpretation device 906 may be embodied as a printed circuit and one or more central processing units for processing a variety of data, one or more random access memory storages for storing data during processing, one or more non-transitory computing unit media storages (such as a hard drive, a solid state drive, and/or a flash memory) for storing computing unit executable programs and data irrespective of the presence of electric power.

Instruction issuance device 904 and/or usage interpretation device 906 may also be embodied as one or more executable steps stored one or more non-transitory computing unit media storages (such as a hard drive, a solid state drive, and/or a flash memory) of computing device 62.

In accordance with one or more embodiments of the present invention, upon insertion of an intubation blade 40 into handle 30, usage interpretation device 906 access usage storage device 902 and determines if the blade has been used before by determining if a usage code has been stored. If the usage code is stored in usage storage device 902, usage interpretation device 906 will cause a computing device 62 to issue a "previously used blade" warning to a user of intubation device 10. This warning may be blinking of display 68, disabling display 68, and/or written and/or pictographic warning on display 68 that intubation blade 40 has been used previously. If a usage code is not stored in usage storage device 902, usage interpretation device 906 will permit computational device 62 to allow a user full functionality of intubation device 10.

In the alternative or in addition, upon insertion of an intubation blade 40 into handle 30, usage interpretation device 906 access usage storage device 902 and determines if the blade has been used before by determining if a non-usage code has been erased or deleted. If a non-usage code is stored in usage storage device 902, usage interpretation device 906 will permit computational device 62 to allow a user full functionality of intubation device 10. If the non-usage code is not stored, e.g., is erased or deleted, in usage storage device 902, usage interpretation device 906 will permit computing device 62 to issue a "previously used blade" warning to a user of intubation device 10. This warning may be blinking of display 68, disabling display 68, and/or written and/or pictographic warning on display 68 that intubation blade 40 has been used previously.

In accordance with one or more embodiments of the present invention, instruction issuance device 904 cause a usage code to be written to the usage storage device 902 when an intubation blade is inserted into handle 30. In the alternative or in addition, instruction issuance device 904 cause a non-usage code to be erased or deleted in the usage storage device 902 when an intubation blade is inserted into handle 30.

Usage code and/or non-usage code may be any suitable code that is used one time or repeatedly and may have any suitable length, be encrypted or unencrypted.

While the present invention has been described at some length and with some particularity with respect to the described embodiments, it is not intended that it should be limited to any such particulars or embodiments or any particular embodiment, but it is to be construed to provide the broadest possible interpretation in view of the prior art and, therefore, to effectively encompass the intended scope of the invention.

What is claimed is:

1. An intubation device for intubating a patient; the intubation device comprising:
    a handle for holding the intubation device by a user;
    a single-use intubation blade, the intubation blade comprising a retainer clip and a lug held fixedly to the intubation blade by the retainer clip, the retainer clip comprising a break-away section;
    a ratchet collar rotatably connected to the handle, the ratchet collar rotatable with respect to the intubation blade in a first travel direction to mount the intubation blade to the handle and in a second travel direction to dismount the intubation blade from the handle;
    a disabling mechanism for preventing re-use of the intubation blade, the disabling mechanism comprising
        a plurality of gear teeth, each gear tooth having a first gear tooth surface disposed substantially perpendicularly to a plane comprising the break-away section;
    wherein when the ratchet collar is rotated to dismount the intubation blade from the handle the first gear tooth surface breaks the break-away section dislocating the lug;
    wherein the ratchet collar comprises
        a mounting channel for directing the lug in the first travel direction and in the second travel direction;
        an entrance to the mounting channel, the entrance disposed at a bottom surface of the ratchet collar for receiving the lug; and
        a seating notch at an end of the mounting channel, the seating notch for seating the lug.

2. The intubation device of claim 1, wherein the handle comprises a first mating portion and the intubation blade comprises a second mating portion, the first mating portion mating with the second mating portion and rotationally locking the handle and the intubation blade.

3. The intubation device of claim 1, further comprising a biasing assembly, the biasing assembly comprising a biasing collar, a spring, and a spring retainer, the biasing assembly for applying a force to seat the lug in the seating notch.

4. The intubation device of claim 1, further comprising an imaging assembly, the imaging assembly comprising
    a lens for acquiring an optical image of a portion of the patient, the lens disposed near a distal end of the intubation blade, the distal end being inserted into the patient;
    an imaging unit for acquiring an electronic image of the portion of the patient from the optical image;
    a display for displaying the electronic image to the user.

5. The intubation device of claim 4, wherein the imaging assembly further comprising
    a conduit lead line and a first connector disposed on the intubation blade, the conduit lead line being connected at one end to the lens and a second end to the first connector,
    a computing unit disposed in the handle, the computing unit comprising the imaging unit and a second connector, the second connector operatively connected with the first connector, to transmit the optical image from the lens to the imaging unit.

6. An intubation device for intubating a patient; the intubation device comprising:
    a handle for holding the intubation device by a user;
    a single-use intubation blade, the intubation blade comprising a retainer clip and a lug held fixedly to the intubation blade by the retainer clip, the retainer dip comprising a break-away section;
    a ratchet collar rotatably connected to the handle, the ratchet collar rotatable with respect to the intubation blade in a first travel direction to mount the intubation blade to the handle and in a second travel direction to dismount the intubation blade from the handle;
    a disabling mechanism for preventing re-use of the intubation blade, the disabling mechanism comprising
        a plurality of gear teeth, each gear tooth having a first gear tooth surface disposed substantially perpendicularly to a plane comprising the break-away section;
    a biasing assembly, the biasing assembly comprising a biasing collar, a spring, and a spring retainer; and
    wherein when the ratchet collar is rotated to dismount the intubation blade from the handle the first gear tooth surface breaks the break-away section dislocating the lug;
    wherein the ratchet collar comprises
        a retention seating notch at an upper end of the ratchet collar for seating a portion of the spring retainer;
    wherein the biasing collar comprises a support edge for supporting the spring; and
    wherein the spring is sandwiched between the spring retainer and the support edge.

7. The intubation device of claim 6, wherein each gear tooth comprises a second gear tooth surface, the second gear tooth surface being substantially parallel to the plane comprising the break-away section.

8. An intubation device for intubating a patient; the intubation device comprising:
    a handle for holding the intubation device by a user;
    a single-use intubation blade, the intubation blade comprising a retainer clip and a lug held fixedly to the intubation blade by the retainer clip, the retainer clip comprising a break-away section;
    a ratchet collar rotatably connected to the handle, the ratchet collar rotatable with respect to the intubation blade in a first travel direction to mount the intubation blade to the handle and in a second travel direction on to dismount the intubation blade from the handle;
    a disabling mechanism for preventing reuse of the intubation blade, the disabling mechanism comprising
        a plurality of gear teeth, each gear tooth having a first gear tooth surface disposed substantially perpendicularly to a plane comprising the break-away section,
    wherein when the ratchet collar is rotated to dismount the intubation blade from the handle the first gear tooth surface breaks the break-away section dislocating the lug,
    wherein the lug comprises an end spring and a tang, and
    wherein the lug is held in an opening in the intubation blade by the end spring and prevented from passing entirely through the opening by the tang.

9. An intubation device for performing an intubation on a patient; the intubation device comprising:
    a handle for holding the intubation device during the intubation;
    a collar fixedly joined to the handle;
    a disposable intubation blade comprising a lug; and
    a ratchet collar rotatably joined to the collar, the ratchet collar comprising a plurality of gear teeth, each gear tooth having a first gear tooth surface;

wherein the ratchet collar is rotatable with respect to the intubation blade to mount the intubation blade in the handle to perform the intubation;

wherein the ratchet collar is rotatable with respect to the intubation blade;

wherein when the ratchet collar is rotated to dismount the intubation blade from the handle, the first gear tooth surface causes the lug to dislodge and permit dismounting of the intubation blade from the handle;

wherein the lug extends through an opening in a wall of the intubation blade into a seating notch in a wall of the ratchet collar to prevent inadvertent removal of the intubation blade during the intubation.

10. The intubation device of claim 9, further comprising an imaging assembly for viewing a portion of the patient during the intubation.

11. The intubation device of claim 10, wherein the imaging assembly comprises a first connector disposed in the handle and a second connector disposed in the intubation blade, the first connector and the second connector operably connecting a lens disposed in the intubation blade and a computing device disposed in the handle.

12. The intubation device of claim 10, wherein a lens is disposed at an end of a channel in the intubation blade.

13. The intubation device of claim 9, wherein the intubation blade further comprises a retainer clip for retaining the lug in the opening of the wall in the intubation blade, the retainer clip comprising a break-away section;

wherein when the break-away section breaks, the lug is dislodged from the opening.

14. An intubation device for intubating a patient; the intubation device comprising:

a single-use intubation blade, the intubation blade comprising a usage storage device comprising a usage code or a non-usage code;

a handle for holding the intubation device by a user, the handle comprising a usage interpretation device for accessing the usage storage device for reading a usage code or a non-usage code to determine if the intubation blade has been used before;

wherein the handle comprising an instruction issuance device for writing the usage code to indicate in a subsequent usage of the intubation blade that the intubation blade has been used previously or deleting the non-usage code to indicate to the user that the intubation blade in a subsequent usage of the intubation blade has been used previously.

* * * * *